(12) United States Patent
Licht et al.

(10) Patent No.: US 11,180,610 B2
(45) Date of Patent: Nov. 23, 2021

(54) METHOD FOR PURIFYING POLOXAMERS

(71) Applicant: MERCK PATENT GMBH, Darmstadt (DE)

(72) Inventors: Anja Licht, Dieburg (DE); Almut Rapp, Darmstadt (DE); Joerg Von Hagen, Pfungstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 544 days.

(21) Appl. No.: 16/085,799

(22) PCT Filed: Feb. 20, 2017

(86) PCT No.: PCT/EP2017/000238
§ 371 (c)(1),
(2) Date: Sep. 17, 2018

(87) PCT Pub. No.: WO2017/157505
PCT Pub. Date: Sep. 21, 2017

(65) Prior Publication Data
US 2019/0085125 A1    Mar. 21, 2019

(30) Foreign Application Priority Data
Mar. 17, 2016    (EP) .................................. 16160811

(51) Int. Cl.
| | | |
|---|---|---|
| *C12N 5/00* | (2006.01) | |
| *C12N 5/02* | (2006.01) | |
| *C08G 65/30* | (2006.01) | |
| *B01J 20/20* | (2006.01) | |
| *B01J 20/28* | (2006.01) | |
| *A61K 48/00* | (2006.01) | |

(52) U.S. Cl.
CPC .............. *C08G 65/30* (2013.01); *B01J 20/20* (2013.01); *B01J 20/28004* (2013.01); *B01J 20/28016* (2013.01); *C12N 5/0018* (2013.01); *C08G 2650/58* (2013.01); *C12N 2500/50* (2013.01)

(58) Field of Classification Search
CPC .. C08G 65/30; C08G 2650/58; C12N 5/0018; C12N 2500/50; B01J 20/20; B01J 20/2804; B01J 20/28016
See application file for complete search history.

(56) References Cited

U.S. PATENT DOCUMENTS

| | | | |
|---|---|---|---|
| 4,677,231 A | | 6/1987 | Aoshima et al. |
| 5,350,714 A | * | 9/1994 | Trefonas, III ............. G03F 7/16 |
| | | | 210/660 |
| 2005/0095221 A1 | | 5/2005 | Balasubramanian et al. |
| 2013/0274421 A1 | | 10/2013 | Kim et al. |
| 2017/0000901 A1 | | 1/2017 | Vissvesvaran et al. |

FOREIGN PATENT DOCUMENTS

| | | |
|---|---|---|
| CN | 103403062 A | 11/2013 |
| CN | 105358674 A | 2/2016 |
| EP | 0181621 A2 | 5/1986 |
| JP | S61120831 A | 6/1986 |
| WO | 2005023896 A2 | 3/2005 |
| WO | 2012091361 A2 | 7/2012 |
| WO | 2015003773 A1 | 1/2015 |
| WO | 2015148736 A1 | 10/2015 |

OTHER PUBLICATIONS

Translation of Office Action dated Jul. 7, 2020 in the corresponding Chinese Examination Procedure 201780017940.3 (pp. 1-11).
International Search Report for PCT/EP2017/000238 dated Apr. 7, 2017.
English Abstract of JPS61120831, Publication Date: Jun. 7, 1986.

* cited by examiner

*Primary Examiner* — Quang Nguyen
(74) *Attorney, Agent, or Firm* — Millen White Zelano and Branigan, PC; Csaba Henter

(57) ABSTRACT

The present invention relates to the purification of poloxamers to be used as cell culture media additives. Activated carbon can be used to remove hydrophobic high molecular weight components which reduce the efficacy of poloxamers as cell culture additives.

17 Claims, 7 Drawing Sheets

METHOD FOR PURIFYING POLOXAMERS

The present invention relates to the purification of poloxamers to be used as cell culture media additives. Activated carbon can be used to remove hydrophobic high molecular weight components which reduce the efficacy of poloxamers as cell culture additives.

BACKGROUND OF THE INVENTION

Poloxamers, especially Poloxamer 188, are used in many industrial applications, cosmetics and pharmaceuticals. They are also used in cell culture media processes. The addition of poloxamers, especially poloxamer 188, to cell culture media improves cell viability significantly. High cell viability is crucial for optimal protein production. Why poloxamers improve cell viability is not fully understood. It is believed that poloxamers reduce shear stress and in this way protect the cells from damage. Poloxamer, being a nonionic surfactant, is likely to concentrate at the gas bubble/medium interface and could prevent cell attachment to gas bubbles and in this way prevent cells from damage when gas bubbles burst. It may also reduce shock when bubbles burst. Some publications claim that poloxamers improve the oxygen transfer rate from the gas into the liquid phase, but other publications contradict these findings. There are also indications that poloxamers may "repair" small defects in cell membranes.

Significant lot-to-lot variability is observed in commercially available poloxamers like poloxamer 188 lots when used in cell culture media. As a consequence some lots are not suitable for the use in cell culture, because they do not protect cells sufficiently from damage/death. The reason for this is still not fully understood. As a consequence cell viability is significantly lower when bad lots are used.

Also for other applications, poloxamers sometimes need to be purified. Several methods of purifying poloxamers have been suggested.

In WO12091361 organometal impurities are identified and removed from poloxamer lots using activated carbon. The removal of organometal impurities is claimed to be necessary to synthesize multiblock copolymers by chain extension to be used as drug delivery system.

In WO2002014380 poloxamer is purified by fractionation. Lower molecular weight components (such as mono- and diblock components) are identified as harmful and are removed by an aqueous two phase extraction process In WO2015148736 a method is described to improve poloxamer performance in cell culture especially for poor performing lots. Temperature treatment was identified to improve the performance of poor performing lots. No clear conclusions were drawn as to why temperature treatment improves the lot or what impurities might be eliminated.

WO2014194137 describes a method to evaluate lot performance of cell culture additives such as poloxamer 188. The presence or absence of high molecular weight components and/or highly hydrophobic components in such additives is indicative of the efficacy of the additive for preventing cellular shear damage.

Still, there is uncertainty about which lots of poloxamers fail to protect cells sufficiently in cell culture, and even more, how those poor performing lots can be treated to turn them into well performing lots.

It has been found that the performance of poor performing poloxamer lots can be increased by treatment with activated carbon. It was further found out that this treatment reduces the amount of high molecular weight hydrophobic compounds in those lots. The more activated carbon is added, the more high molecular weight component is removed (see SEC data) and the better the performance in cell culture is (see viability increase in cell culture).

The present invention is thus directed to a method for increasing the efficacy of poloxamers to increase cell viability in cell culture by
a) Providing the poloxamers whose efficacy shall be improved
b) Dissolving the poloxamers of step a) in a solvent and contacting them with activated carbon
c) Removing the activated carbon and the solvent to obtain the poloxamer with improved efficacy It is obvious to a person skilled in the art that lots which show optimal efficacy cannot be further improved. Poloxamers whose efficacy shall be improved are those whose efficacy to increase cell viability in cell culture is lower than those of other poloxamer lots. This can for example be tested in a cell viability assay. An example of a suitable assay and its application is provided in Example 6.

In a preferred embodiment, the solvent is water, acetone, THF or a mixture of ethanol and water.

In another preferred embodiment the dissolved poloxamers are contacted with activated carbon for 1 minute to 24 hours depending on whether it is done in flow through or batch.

In another preferred embodiment, in step c), activated carbon is removed by centrifugation and/or filtration.

In a preferred embodiment the poloxamers provided in step a) comprise components that have a molecular weight over 13,000 g/mol determined by SEC.

In a preferred embodiment the poloxamers are poloxamer which have an average molecular weight between 7680 and 9510 g/mol as defined in the pharmacopeia for poloxamer 188 and determined according to pharmacopeia by titration using a phthalic anhydride-pyridine solution.

In another embodiment the activated carbon is an activated carbon obtained by pyrolysis of an organic polymeric material, preferably polystyrene.

The present invention is further directed to a method for removing hydrophobic, high molecular weight components from of poloxamers by dissolving them in a solvent and contacting the solution with activated carbon. Afterwards the solvent and the activated carbon are removed.

The present invention is further directed to a method for performing cell culture by culturing cells in an aqueous culture medium comprising poloxamers that prior to adding them to the cell culture medium have been treated by the method for increasing the efficacy of poloxamers to increase cell viability in cell culture as described above.

The present invention is thus also directed to a method for performing cell culture by culturing cells in an aqueous culture medium comprising poloxamers that prior to adding them to the cell culture medium have been treated by
a) Dissolving the poloxamers in a solvent and contacting them with activated carbon
b) Removing the activated carbon and the solvent In a preferred embodiment, the solvent is water, acetone, THF or a mixture of ethanol and water.

In another preferred embodiment the dissolved poloxamers are contacted with activated carbon for 1 minute to 24 hours.

In another preferred embodiment, in step c), activated carbon is removed by centrifugation and/or filtration.

In a preferred embodiment the poloxamers provided in step a) comprise components that have a molecular weight over 13,000 g/mol determined by SEC.

In a preferred embodiment the poloxamers are poloxamer which have an average molecular weight between 7680 and 9510 g/mol as defined in the pharmacopeia for poloxamer 188 and determined according to pharmacopeia by titration using a phthalic anhydride-pyridine solution.

In another preferred embodiment the activated carbon is an activated carbon obtained by pyrolysis of an organic polymeric material, preferably polystyrene.

Figure 1:
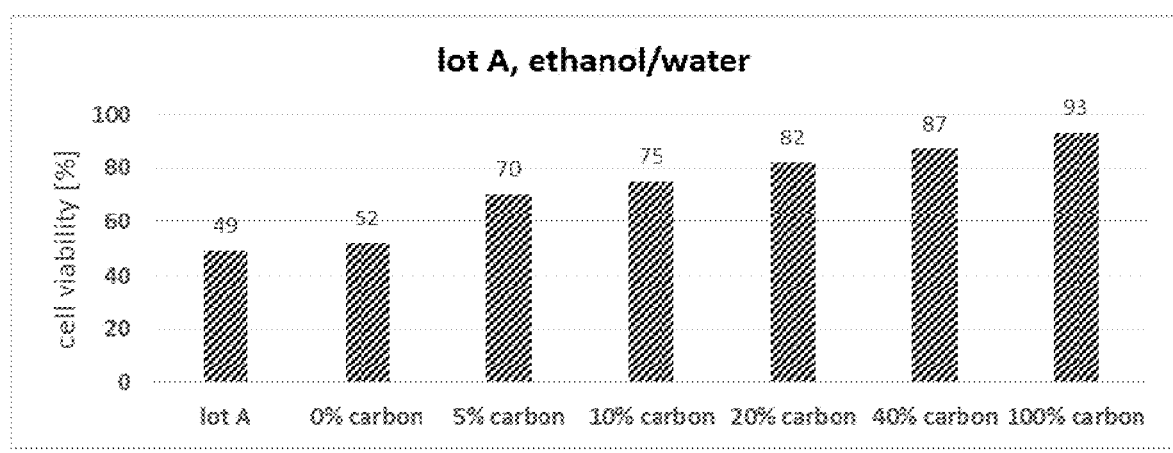
FIG. 1: Cell viability of poor performing lot A and after purification with 0, 5, 10, 20, 40 and 100 wt. % activated carbon in ethanol/water as described in example 2 and 6b. 0% carbon corresponds to blank value. The minor deviation of the blank value to lot A is within the error margin of the measurement.

Further details concerning the Figures can be found in the Examples.

Definitions

Before describing the present invention in detail, it is to be understood that this invention is not limited to specific compositions or process steps, as such may vary. It must be noted that, as used in this specification and the appended claims, the singular form "a", "an" and "the" include plural referents unless the context clearly dictates otherwise. Thus, for example, reference to "a poloxamer" includes a plurality of poloxamers. and the like. Unless defined otherwise, all technical and scientific terms used herein have the same meaning as commonly understood by one of ordinary skill in the art to which this invention is related. The following terms are defined for purposes of the invention as described herein.

The term "bioreactor," as used herein, refers to any manufactured or engineered device or system that supports a biologically active environment. In some instances, a bioreactor is a vessel in which a cell culture process is carried out which involves organisms or biochemically active substances derived from such organisms. Such a process may be either aerobic or anaerobic. Commonly used bioreactors are typically cylindrical, ranging in size from liters to cubic meters, and are often made of stainless steel. In some embodiments described herein, a bioreactor might contain a disposable constituent made of a material other than steel and is disposable. In some embodiments that is a disposable bag where in the biologically active environment is maintained. It is contemplated that the total volume of a bioreactor may be any volume ranging from 100 mL to up to 10,000 Liters or more, depending on a particular process.

A high molecular weight, hydrophobic component or compound comprised in a poloxamer according to the present invention is a component that is more hydrophobic than the target poloxamer according to the specification in which it is comprised and that has a higher molecular weight than the average molecular weight of the poloxamer in which it is comprised. The component is more hydrophobic if it is removed from the poloxamer by treatment with activated carbon according to the present invention. The higher molecular weight can be shown e.g. by SEC.

Preferably, the high molecular weight, hydrophobic component is a poloxamer with higher molecular weight and a higher PPO/PEO ratio than the poloxamer according to the specification, like e.g. Poloxamer 188. SEC-FTIR measurements identified the high molecular weight component to also typically be a poloxamer type block copolymer. This shows that a poor performance of a poloxamer lot in cell culture can be attributed to the presence of a more hydrophobic and higher molecular weight poloxamer component (e.g. in case of poloxamer 188 being the target poloxamer according to the specification it is a poloxamer with higher molecular weight and a higher PPO/PEO ratio than poloxamer 188).

Average molecular weight according to pharmacopeia is determined by titration using a phthalic anhydride-pyridine solution.

Average molecular weight determined by SEC is determined as follows:

weight average molecular weight: $M_w = \Sigma_i N_i M_i^2 / (\Sigma_i N_i M_i)$ number average molecular weight: $M_n = \Sigma_i N_i M_i / (\Sigma_i N_i)$ peak molecular weight: $M_p$ = molecular weight at maximum $N_i$ $N_i$ = number of polymer species in fraction i
$M_i$ = molecular weight of polymer species in fraction i
SEC conditions:
Calibration standards: PEG (details see example 7)
Eluent: THF
Flow rate: 1 ml/min
Injection volume: 100 µl
Column: particle size=5 µm, material=styrene-divinylbenzene
Temperature: 40° C.

DETAILED DESCRIPTION OF THE INVENTION

The gist of the present invention is the finding that the suitability of poloxamers as enhancers of cell viability depends on the presence or absence of hydrophobic, high molecular weight compounds and that those hydrophobic, high molecular weight compounds can be removed by contacting the solubilized poloxamer with activated carbon.

Activated carbon is a material having extensive non-specific adsorption properties, and is used as an adsorbent or as a decolorant in the industrial fields, such as the production of chemicals and foods, sewage or waste water treatment, water filtration, and production of small-molecule drugs.

The term "active carbon" or "activated carbon" or "activated charcoal" as used interchangeably herein, refers to a carbonaceous material which has been subjected to a process to enhance its pore structure. Activated carbons are porous solids with very high surface areas. They can be derived from a variety of sources including coal, wood, coconut husk, nutshells, peat and also organic polymers. Activated carbon can be produced from these materials using physical activation involving heating under a controlled atmosphere or chemical activation using strong acids, bases, or oxidants. The activation processes produce a porous structure with high surface areas that give activated carbon high capacities for impurity removal. Activation processes can be modified to control the acidity of the surface.

It has been found that activated carbon that has been obtained from organic polymers is also suitable for removing hydrophobic, high molecular weight compounds according to the present invention. Organic polymers are any synthetic, chemically defined organic polymers, like e.g. polystyrene, polyamide, polycarbonate, polymethylpentene, polyethylene, polyesters, polyvinyls or polypropylene.

The activated carbon may comprise or consist of spherical active carbon particles. That means they have essentially similar extensions in all three spatial dimensions. Besides the spherical shape, cubical, parallelepiped or cylindrical shapes are imaginable, provided that the extensions in two different spatial dimensions do not differ by more than a factor 3, preferably less than a factor 2.

The activated carbon obtained from organic polymers can be produced by pyrolysis of spherical organic material, for example polystyrene. However, it is also possible to pyrolyze glucose solutions, as described in Int. J. Electrochem. Sci., Vol. 4, 2009, pages 1063 to 1073. The manufacture of spherical activated carbon is further disclosed in US 20060148645 and US 2008171648.

An exemplary way of manufacturing such active carbon polymer particles is to use polymer balls, in particular ion exchanger balls, the polymer structure of which contains separable functional groups, in particular sulfonyl groups and/or carboxyl groups, as an educt. The porous polymer balls are pyrolyzed, and optionally the pyrolyzed polymer balls are subjected to an activation step. The separation of the functional groups preferably occurs up to a residual content (referred to the weight share of the functional groups, as used) of 5% to 15%. The temperature of this first heat treatment is suitably in the range from 200° C. to 350° C. for 10 min to 60 min. The atmosphere is in principle arbitrary. The following pyrolysis step starts at a temperature, which essentially corresponds to the final temperature of the first heat treatment, and preferably ends at 600° C. to 800° C. The heating-up rate is suitably in the range from 5 K/min to 0.5 K/min, and therefrom the duration of the pyrolysis step can immediately be calculated. The activation step is uncritical and occurs in a conventional way.

Suitable activated carbon is e.g. CAS 7440-44-0, a suitable spherical activated carbon is AK 1500 (Felgenträger).

Suitable spherical activated carbons are also available as SARATECH™ 100562, SARATECH™ 100772 and SARATECH™ 101373 (Blücher GmbH, Erkrath, Germany).

The activated carbon has a surface area of preferably 10 to 10 000 m²/g, more preferably of 100 to 5000 m²/g, most preferably of 300 to 2000 m²/g.

The mean particle size of the activated carbon is preferably at least 2 µm, more preferably from 2 to 800 µm.

Characterization of particles is known in the art and preferably made by sieving. This is described by: I. C. Edmundson, Particle-size analysis, H. S. Bean, A. H. Beckett and J. E. Caries (eds) in: Advances in Pharmaceutical Sciences vol. 2, Academic Press, London 1967, 95-174.

The mean particle size of the product fraction may be determined by means of EDANA recommended test method No. WSP 220.2-05 "Particle Size Distribution", where the proportions by mass of the screen fractions are plotted in cumulated form and the mean particle size is determined graphically. The mean particle size here is the value of the mesh size which gives rise to a cumulative 50% by weight.

The proportion of activated carbon having a certain particle size range, e.g. of 2 to 800 µm, is preferably at least 90% by weight, more preferably at least 95% by weight, most preferably at least 98% by weight of the whole activated carbon.

A poloxamer is a polyethylene glycol (PEG)/polypropylene glycol (PPG) tri-block copolymer.

The poloxamers, CAS number 9003-11-6, have the general formula I

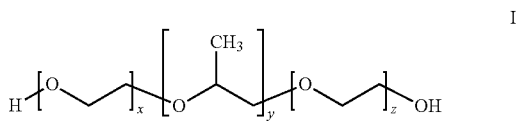

with x and z preferably independently being 5 to 150 and y preferably being 15 to 67.

They are commercially available (Pluronics® or Lutrole®, e.g., a Pluronic® solution, gel, or solid, such as Pluronic® F-68). Alternatively, the poloxamer can be made from raw materials according to methods known in the art (see, for example, U.S. Pat. Nos. 3,579,465 and 3,740,421).

Further information about poloxamers can be found in Hagers Handbuch der Pharmazeutischen Praxis, volume 9 "Stoffe P-Z", 1994, pages 282 to 284.

In a preferred embodiment, the poloxamer to be purified and used according to the present invention is Poloxamer 188. Poloxamer 188 has an average molecular weight between 7680 and 9510 g/mol (defined and determined according to pharmacopeia). In formula I, for Poloxamer 188 x and z are around 80 and y is around 27. This compound is commercially available as Poloxamer 188, Pluronic® F 68, Kolliphor® P 188, Lutrol® F 68, SYNPERONIC™ PE/F 68 or PLONON #188P.

A person skilled in the art knows how to use poloxamers as ingredients in cell culture media. He is aware of the suitable amount and format to use. But sometimes, cell culture, even if it was prepared according to standard procedures and recipe, does not perform as good as it typically does. It has been found that this might be due to the poloxamer. In such a case, until now the whole lot of poloxamer had to be discarded. The present invention provides a simple and efficient method to purify such poor lots so that they can be used as cell culture ingredient after purification.

The identification of a lot of poloxamer that does not perform as well as expected can be e.g. done in cell culture. If a cell culture comprising poloxamer does not show a cell viability and performance as expected one might try to improve this by purifying the poloxamer prior to use by incubating it with activated carbon according to the present invention.

Any cell culture that does not perform as expected can trigger a purification of the poloxamer according to the present invention. It is also possible to do cell culture tests in advance of the actual cell culture. An experimental set-up to investigate the performance of the cell culture could be as follows:

A suitable experimental set-up is the small scale baffled shake flask model described in Haofan Peng et al., Biotechnol. Frog., 2014, Vol. 30 (6), 1411-1418. Further details can be found in Example 6.

To a skilled person it is obvious that:
- different concentrations of poloxamer can be used (typically between 0.1 and 5 g/L)
- any type of CHO cells or other cells can be used
- any type of cell culture medium suitable for the chosen cell line can be used
- cultivation takes preferably place on an orbital shaker and speed and throw may need to be adjusted to the chosen cell line and cultivation conditions.
- depending on chosen parameters described above, viability drop may be measured at a suitable time point between 2 hours and 5 days.

The definition of cell viability according to the present invention is the percentage of living cells in a solution as determined by e.g. a Trypan blue assay in a Beckman-Coulter ViCell XR or similar.

As we have found out that the components which are responsible for the poor performance are high molecular weight, hydrophobic components, it is also possible to analyze each lot of poloxamer prior to its use. If high molecular weight, hydrophobic components are present, the lot is purified prior to use by incubating it with activated carbon according to the present invention. The analysis can e.g. be performed by SEC (size exclusion chromatography).

For the contact with the activated carbon the poloxamer needs to be dissolved in a solvent.

Any solvent or solvent mixture that dissolves poloxamers, especially poloxamer 188, and can be removed afterwards can be used and is a suitable solvent. A clear solution should be obtained but slight turbidities are acceptable. It is advisable to choose a solvent that can be easily evaporated as it needs to be removed afterwards. In case of e.g. water as a solvent poloxamer can by lyophilized or spray dried. Preferred solvents are acetone, acetonitrile, DMSO, ethanol, methanol, THF, acetonitrile and water or mixtures thereof, like a mixture of water and ethanol.

The addition of small amounts of water to other solvents can improve the solubility of the poloxamer. It is also possible to use higher amounts of solvent compared to the amount of poloxamer to reduce turbidity, to reduce viscosity etc. As long as the poloxamer is sufficiently dissolved, the amount of solvent is typically not critical as it is removed after the treatment with activated carbon.

In the following some examples of suitable solvents and the amount needed are given.

The minimum amount of solvent that needs to be used per g poloxamer 188 is defined by the minimum amount needed to dissolve poloxamer.

Examples of solvents and typical amounts needed to dissolve 1 g of poloxamer 188 are as follows:

Water: ≥6.5 ml (very viscous at 6.5 ml/g→larger amounts of water recommended to reduce viscosity)
THF: 50 ml/g→clear solution
Methanol: 80 ml/g→clear solution
Acetonitrile: 30 ml/g→slight turbidity 40 ml/g→clear solution
DMSO: 60 ml/g→slight turbidity
(60 ml DMSO+800 µl water)/g→clear solution
Acetone: 60 ml/g→slight turbidity
(60 ml acetone+800 µl water)/g→clear solution
Ethanol: (50 ml ethanol+1 ml water)/g→clear solution
Propanol: (120 ml propanol+6 ml water)/g→clear solution
1-Butanol: (150 ml 1-butanol+8 ml water)/g→clear solution
2-Butanol: (150 ml 2-butanol+9 ml water)/g→clear solution 2-methyl-1-propanol: (150 ml 2-methyl-1-propanol+7 ml water)/g→clear solution The solution comprising the dissolved poloxamer is then contacted with the activated carbon. It is also possible to first mix the activated carbon with the solvent and afterwards add the poloxamer. Incubation of the solubilized poloxamer with activated carbon can be done batch-wise or continuously. The contact time of the mixture comprising the solvent, the poloxamer and activated carbon is typically between 1 minute and 24 hours. If the incubation is done in a batch mode it is preferably performed between 3 hours and 15 hours.

If the contacting is performed continuously by flowing the liquid containing the poloxamer through the activated carbon, the contact time is typically between 1 minute and 30 minutes. For this the activated carbon might be packed in a column, a cartridge, a filter or any other suitable device.

Preferably, the residence time of the liquid in the device is between 1 and 10 minutes. A suitable system for performing a continuous purification is the Stax AKS Sytem (Pall).

If the incubation is done batch-wise, the components are mixed and the mixture is preferably agitated during contact time, e.g. by stirring or shaking. Typically, the incubation of the suspension is done at room temperature.

The amount of activated carbon can be adjusted according to the amount of high molecular weight components that needs to be removed. It has been found that the more high molecular weight components need to be removed, the more activated carbon needs to be used. Typically, the activated carbon is used in amounts between 1:1 and 1:10 (weight of activated carbon:weight of poloxamer).

Afterwards, activated carbon is removed from the suspension. Separating the liquid from the activated carbon can e.g. be done by sedimentation, centrifugation and/or preferably filtration. Typically, two or more filtration steps are used to remove the activated carbon as completely as possible. A person skilled in the art is able to adjust the pore size of the filter to the particle size of the activated carbon.

After removing the activated carbon, the liquid is removed from the solution comprising the poloxamer. This can be done e.g. by evaporation, spray drying or lyophilisation.

Evaporation is preferably done under reduced pressure at moderate temperatures. Evaporation is typically carried out with distillation type equipment. In small scale it is easily carried out with a rotational evaporator. Typical conditions are e.g.:

Acetone: 555 hPa, 40° C.
Acetonitrile: 240 hPa, 40° C.
THF: 355 hPA, 40° C.
Ethanol: 175 hPa, 40° C.
Methanol: 335 hPa, 40° C.
Water: 70 hPA, 40° C.

If the temperatures are below or above 40° C., pressure needs to be adjusted accordingly. Prolonged exposure to temperatures above 50° C. should be avoided.

Additional drying can be carried out in an oven or vacuum oven, if necessary.

For lyophilization or freeze drying the material is frozen in e.g. liquid nitrogen and solvent is sublimated by reducing the surrounding pressure.

The purified and dried poloxamer can then be used in cell culture. If its particle size needs to be adjusted, it can optionally be milled prior to adding it to the cell culture medium.

A cell culture is any setup in which cells are cultured.

A cell culture can be performed in any container suitable for the culture of cells, such as a petri dish, contact plate, bottle, tube, well, vessel, bag, flask and/or tank. Preferably, it is performed in a bioreactor. Typically the container is sterilized prior to use. Culturing is typically performed by incubation of the cells in an aqueous cell culture medium under suitable conditions such as suitable temperature, osmolality, aeration, agitation, etc. which limit contamination with foreign microorganisms from the environment. A person skilled in the art is aware of suitable incubation conditions for supporting or maintaining the growth/culturing of cells.

A cell culture medium (synonymously used: culture medium) according to the present invention is any mixture of components which maintains and/or supports the in vitro growth of cells and/or supports a particular physiological state. It is also suitable for pre-enrichment cultures as well as for use as a maintenance medium.

Preferably, it is a chemically defined medium. The cell culture medium can comprise all components necessary to maintain and/or support the in vitro growth of cells or be used for the addition of selected components in combination with or not in combination with further components that are added separately (media supplement). Preferably, the cell culture medium comprises all components necessary to maintain and/or support the in vitro growth of cells.

A cell culture medium which comprises all components necessary to maintain and/or support the in vitro growth of cells typically comprises at least one or more saccharide components, one or more amino acids, one or more vitamins or vitamin precursors, one or more salts, one or more buffer components, one or more co-factors and one or more nucleic acid components (nitrogenous bases) or their derivatives. It may also comprise chemically defined biochemicals such as recombinant proteins, e.g. rinsulin, rBSA, rTransferrin, rCytokines etc.

Cell culture media can be in the form of aqueous liquids or in the form of dry powders which for use are dissolved in water or an aqueous buffer.

A person skilled in the art is able to choose a suitable cell culture medium for the specific envisaged purpose.

The experimental data show that only poloxamer 188 lots with high molecular weight components that are more hydrophobic than poloxamer 188 (typically due to higher PPO/PEO ratio) have a negative effect on cell viability and can be removed with activated carbon.

Figure 3:
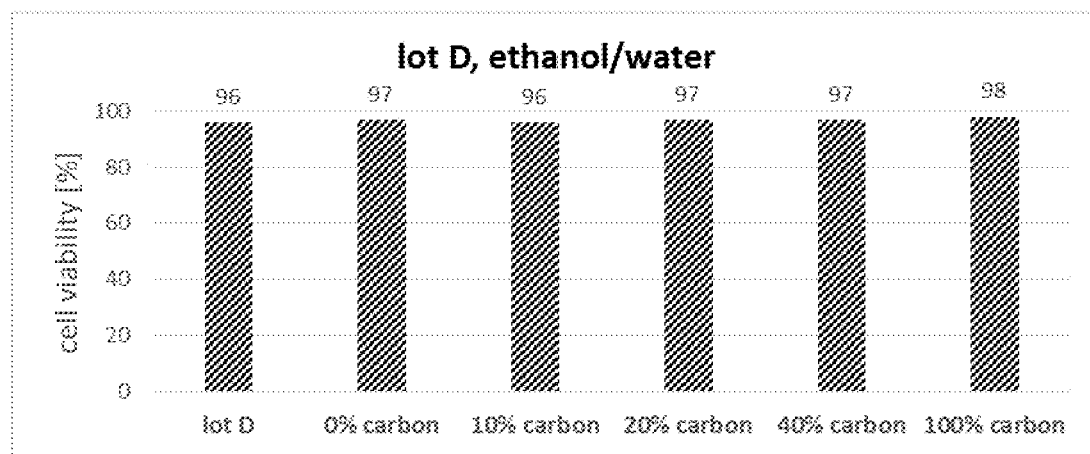
FIG. 3: Cell viability of good performing lot D and after treatment with 0, 10, 20, 40 and 100 wt. % activated carbon in ethanol/water as described in example 2 and 6b. 0% carbon corresponds to blank value. The minor deviation of the blank value to lot D is within the error margin of the measurement.
Figure 7:
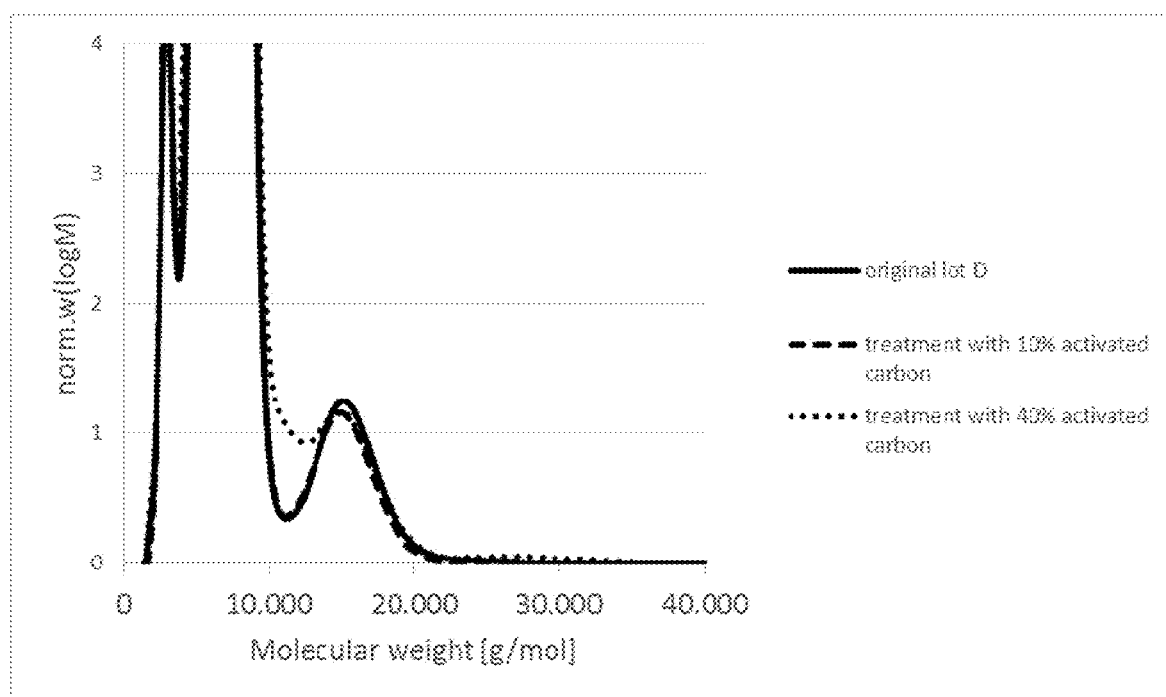
FIG. 7: Size exclusion chromatogram (zoomed in) of well performing lot D (solid line) and after treatment with 10 and 40 wt. % activated carbon in ethanol/water (dashed lines) as described in example 2. Small deviations observed for 40% activated carbon at ~11 000 g/mol can be attributed to residual activated carbon (not completely removed).

High molecular weight components with a molecular weight between around 13000 and 50000 g/mol with similar hydrophobicity as e.g. poloxamer 188 (similar PPO/PEO ratio) have no negative effect on cell viability and cannot be removed by activated carbon (FIGS. 3 and 7). Considering the fact that poloxamers are amphiphilic polymers, with two hydrophilic blocks and a hydrophobic block in the middle, it is somewhat surprising that activated carbon is actually capable of selectively adsorbing the more hydrophobic, higher molecular weight poloxamer components, while much less adsorption of the actual poloxamer (e.g. poloxamer 188) takes place. This allows a successful purification of poloxamers suitable for cell culture with good yields.

Based on the amount of activated carbon that is used, especially if activated carbon is used in excess, the method of the invention is suitable to remove at least 50%, preferably at least 75%, most preferred at least 90% of the hydrophobic, high molecular weight components from the poloxamer while typically more than 80% preferably at least 90% of the target poloxamer can be regained after the treatment with activated carbon.

The entire disclosures of all applications, patents, and publications cited above and below, as well as of corresponding patent application EP 16160811.2 filed Mar. 17, 2016, are hereby incorporated by reference.

EXAMPLES

Example 1

Purification of Poloxamer with Activated Carbon in Water

Activated carbon was added to 195 g of deionized water (see table below for amount of activated carbon added). 5.0 g poloxamer 188, each were added to the suspension (see table below). After mixing the suspension overnight, it was filtered through a Pall VacuCap® (0.2 μm) to remove activated carbon. The filtrate was lyophilized.

| Poloxamer 188 lot | Poloxamer 188 [g] | activated carbon [g] | activated carbon [% w/w] |
|---|---|---|---|
| A | 5.0 | 0.0 | 0 |
| A | 5.0 | 1.0 | 20 |
| B | 5.0 | 0.0 | 0 |
| B | 5.0 | 1.0 | 20 |
| C | 5.0 | 0.0 | 0 |
| C | 5.0 | 1.0 | 20 |
| D | 5.0 | 0.0 | 0 |
| D | 5.0 | 1.0 | 20 |

Example 2

Purification with Activated Carbon in Ethanol/Water 5.0 g poloxamer 188 were added to 195 g ethanol, each. 2.5 wt % water, each were added to dissolve poloxamer 188. After 1 hour of mixing activated carbon was added (see table below):

| Poloxamer 188 lot | Poloxamer 188 [g] | activated carbon [g] | activated carbon [% w/w] |
|---|---|---|---|
| A | 5.0 | 0.0 | 0 |
| A | 5.0 | 0.25 | 5 |
| A | 5.0 | 0.5 | 10 |
| A | 5.0 | 1.0 | 20 |
| A | 5.0 | 2.0 | 40 |
| A | 5.0 | 5.0 | 100 |
| B | 5.0 | 0.0 | 0 |
| B | 5.0 | 0.5 | 10 |
| B | 5.0 | 1.0 | 20 |
| B | 5.0 | 2.0 | 40 |
| B | 5.0 | 5.0 | 100 |
| C | 5.0 | 0.0 | 0 |
| C | 5.0 | 1.0 | 20 |
| D | 5.0 | 0 | 0 |
| D | 5.0 | 0.5 | 10 |

-continued

| Poloxamer 188 lot | Poloxamer 188 [g] | activated carbon [g] | activated carbon [% w/w] |
|---|---|---|---|
| D | 5.0 | 1.0 | 20 |
| D | 5.0 | 2.0 | 40 |
| D | 5.0 | 5.0 | 100 |

After mixing the suspension overnight, it was filtered through a frit P4 with a 2.5 µm filter (Art-Nr. 1005-070, Whatman, 2.5 µm pore size). Residual carbon in the filtrate was removed by a second filtration using a suction filter with a 2.5 µm filter (Art-Nr. 1005-070, Whatman, 2.5 µm pore size). Solvent was evaporated on a rotational evaporator until poloxamer was dry.

Example 3

Purification with Spherical Activated Carbon in Ethanol/Water

To a solution of 5.0 g poloxamer 188 in ethanol/water (97.5:2.5) the following amounts of spherical activated carbon (Felgentrager, surface area: 1000-2000 $m^2$/g, particle size: 0.3-0.8 mm) were added (see table below):

| Poloxamer 188 lot | Poloxamer 188 [g] | spherical activated carbon [g] | spherical activated carbon [% w/w] |
|---|---|---|---|
| A | 5.0 | 0.0 | 0 |
| A | 5.0 | 1.0 | 20 |
| A | 5.0 | 5.0 | 100 |
| B | 5.0 | 0.0 | 0 |
| B | 5.0 | 1.0 | 20 |
| B | 5.0 | 5.0 | 100 |

After mixing overnight the suspension was filtered through a frit P4 with a 2.5 µm filter (Art-Nr. 1005-070, Whatman, 2.5 µm pore size). A second filtration was not necessary because spherical activated carbon was easily removed in one filtration step. Solvent was evaporated on a rotational evaporator until poloxamer was dry.

Example 4

Purification with Activated Carbon in THF 5.0 g poloxamer 188 were dissolved in 250 ml THF. The following amounts of activated carbon were added:

| Poloxamer 188 lot | Poloxamer 188 [g] | activated carbon [g] | activated carbon [% w/w] |
|---|---|---|---|
| A | 5.0 | 0.0 | 0 |
| A | 5.0 | 5.0 | 100 |

After mixing the suspension overnight, it was filtered through a frit P4 with a 2.5 µm filter (Art-Nr. 1005-070, Whatman, 2.5 µm pore size). Residual carbon in the filtrate was removed by a second filtration using a suction filter with a 2.5 µm filter (Art-Nr. 1005-070, Whatman, 2.5 µm pore size). Solvent was evaporated on a rotational evaporator until poloxamer was dry.

Example 5

Purification with Activated Carbon in Acetone 5.0 g poloxamer 188 were dissolved in 300 ml acetone. The following amounts of activated carbon were added:

| Poloxamer 188 lot | Poloxamer 188 [g] | activated carbon [g] | activated carbon [% w/w] |
|---|---|---|---|
| A | 5.0 | 0.0 | 0 |
| A | 5.0 | 1.0 | 20 |
| A | 5.0 | 5.0 | 100 |

After mixing the suspension overnight, it was filtered through a frit P4 with a 2.5 µm filter (Art-Nr. 1005-070, Whatman, 2.5 µm pore size). Residual carbon in the filtrate was removed by a second filtration using a suction filter with a 2.5 µm filter (Art-Nr. 1005-070, Whatman, 2.5 µm pore size). Solvent was evaporated on a rotational evaporator until poloxamer was dry.

Example 6

Cell Viabilities Determined with a Small Scale Cell Assay

The cell assay was carried out similar to Haofan Peng et al., Biotechnol. Prog., 2014, Vol. 30 (6), 1411-1418. The cell culture is performed in baffled shake flasks to induce shear forces that potentially damage the cells. CHO-S cells and Cellvento™ CHO-220 medium are used. The poloxamer concentration is 1 g/L. The cell culture medium is inoculated with the cells of choice at a viable cell density of about 1 million cells/mL. Cultivation takes place in an orbitally shaken incubator. Cell viability (percentage of living cells in a solution) is determined after 4 h by a trypan blue assay in a Beckman-Coulter ViCell XR. Each lot is measured in triplicates. The following average cell viabilities were determined for poloxamer 188 lots A, B, C and D:

| Poloxamer 188 lot | cell viability [%] |
|---|---|
| A | 49 |
| B | 87 |
| C | 40 |
| D | 96 |

Poloxamer 188 lots A and C are very poor performing lots, lot B is a medium performing lot and lot D is a good performing lot. In general >90% is considered to be a sufficiently good viability.

Example 6a

Cell Viabilities Using Purified Poloxamer Lots Described in Example 1

Cell assay carried out as described in example 6. Performance of purified poloxamer lots described in example 1:

| Poloxamer 188 lot | activated carbon [% w/w] | cell viability [%] | Improvement of viability after purification [%] |
|---|---|---|---|
| A | 0 | 51 | blank value |
| A | 20 | 71 | 45 |
| B | 0 | 86 | blank value |
| B | 20 | 99 | 14 |
| C | 0 | 38 | blank value |
| C | 20 | 95 | 138 |
| D | 0 | 97 | blank value |
| D | 20 | 98 | 1* |

*within error margin of measurement

The worse the performance of the original lot (the lower the cell viability), the more pronounced the improvement of cell viability after purification using 20 wt. % activated carbon in water. Cell viability for poor performing lots A and C improves by 45% and 138%, respectively. Cell viability for medium performing lot B improves by 14%. Treatment of good performing lot D with 20 wt % activated carbon has no effect, since there is nothing to purify.

Example 6b

Cell Viabilities Using Purified Poloxamer Lots Described in Example 2

Assay carried out as described in example 6. Performance of purified poloxamer lots described in Example 2:

| Poloxamer 188 lot | activated carbon [g] | cell viability [%] | Improvement of viability after purification [%] |
|---|---|---|---|
| A | 0 | 52 | blank value |
| A | 5 | 70 | 43 |
| A | 10 | 75 | 53 |
| A | 20 | 82 | 67 |
| A | 40 | 87 | 78 |
| A | 100 | 93 | 90 |
| B | 0 | 86 | blank value |
| B | 10 | 89 | 2 |
| B | 20 | 92 | 6 |
| B | 40 | 92 | 6 |
| B | 100 | 97 | 11 |
| C | 0 | 44 | blank value |
| C | 20 | 70 | 75 |
| D | 0 | 97 | blank value |
| D | 10 | 96 | 1* |
| D | 20 | 97 | 0 |
| D | 40 | 97 | 0 |
| D | 100 | 98 | 2* |

*within error margin of measurement

Figure 2:
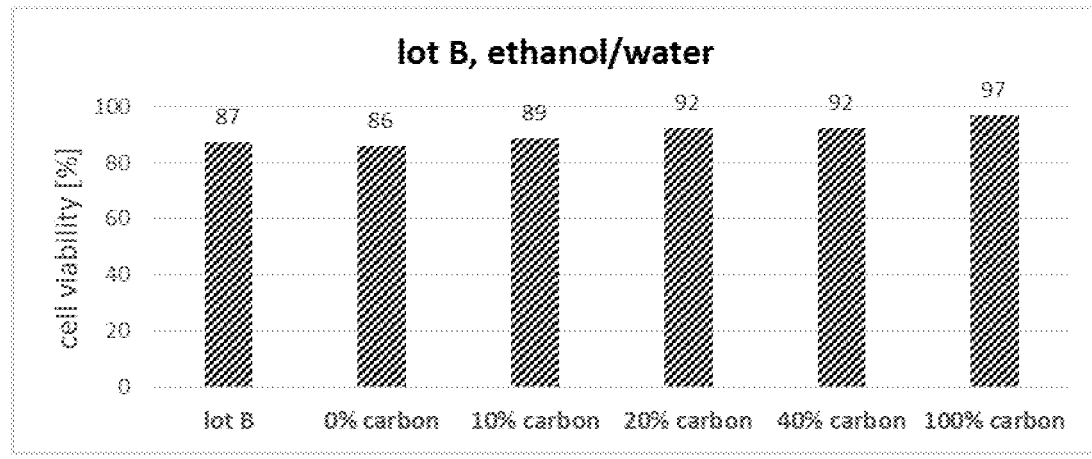
FIG. 2: Cell viability of medium performing lot B and after purification with 0, 10, 20, 40 and 100 wt. % activated carbon in ethanol/water as described in example 2 and 6b. 0% carbon corresponds to blank value. The minor deviation of the blank value to lot B is within the error margin of the measurement.

The poorer the original lot performs in cell culture (the worse the cell viability), the more activated carbon is necessary for purification to achieve a good viability of >90%. For very poor performing lot A (49% viability) 100 wt. % activated carbon are needed to purify the lot sufficiently to achieve >90% cell viability (see also FIG. 1). For medium performing lot B (87% viability) only 20 wt. % activated carbon need to be used for purification to achieve >90% cell viability (see also FIG. 2). Performance of lot D is very good with 96% viability. A treatment with activated carbon has no effect on the performance of the lot (minor deviation between the samples are within error of measurement), see also FIG. 3. This implies that the high molecular weight component in poloxamer lot D is not hydrophobic and is thus not removed by activated carbon. SEC data supports these findings (FIG. 7).

Example 6c

Cell Viabilities Using Purified Poloxamer Lots Described in Example 3

Assay carried out as described in example 6. Performance of purified poloxamer lots described in example 3:

| Poloxamer 188 lot | spherical activated carbon [% w/w] | cell viability [%] | Improvement of viability after purification [%] |
|---|---|---|---|
| A | 0 | 47 | blank value |
| A | 20 | 83 | 69 |
| A | 100 | 99 | 102 |
| B | 0 | 85 | blank value |
| B | 20 | 90 | 3 |
| B | 100 | 98 | 13 |

The improvement of poor performing poloxamer lots through treatment with activated carbon is similar for spherical activated carbon and standard activated carbon (see example 6b). Purification using 100 wt % spherical activated carbon results in cell viabilities of 99 and 98% for lot A and B, respectively. This corresponds to an improvement of more than 100% for lot A and 13% for lot B.

Example 6d

Cell Viabilities Using Purified Poloxamer Lots Described in Example 4

Assay carried out as described in example 6. Performance of purified poloxamer lots described in example 4:

| Poloxamer 188 lot | activated carbon [% w/w] | cell viability [%] | Improvement of viability after purification [%] |
|---|---|---|---|
| A | 0 | 46 | blank value |
| A | 100 | 95 | 94 |

Purification of very poor performing lot A with 100 wt % activated carbon in THF results in a significant improvement of cell viability, similar to purifications carried out in e.g. water or ethanol/water (see examples 6a-6c).

Example 6e

Cell Viabilities Using Purified Poloxamer Lots Described in Example 5

Assay carried out as described in example 6. Performance of purified poloxamer lots described in example 5:

| Poloxamer 188 lot | activated carbon [% w/w] | cell viability [%] | Improvement of viability after purification [%] |
|---|---|---|---|
| A | 0 | 52 | blank value |
| A | 20 | 63 | 29 |
| A | 100 | 79 | 61 |

Purification of very poor performing lot A with activated carbon in acetone results in a significant improvement of cell viability but not as pronounced as in e.g. water, ethanol/water or THF (see examples 6a-d).

Example 7

All size exclusion chromatography (SEC) measurements are carried out as follows:
Calibration standards: PEG (Mp: 430, 982, 1960, 3020, 6690, 12300, 26100 and 44 000 g/mol)
Eluent: THF
Flow rate: 1 ml/min
Injection volume: 100 µl
Column: particle size=5 µm, material=styrene-divinylbenzene
Temperature: 40° C.
Detector: refractive index (RI)

Example 7a

Figure 4:
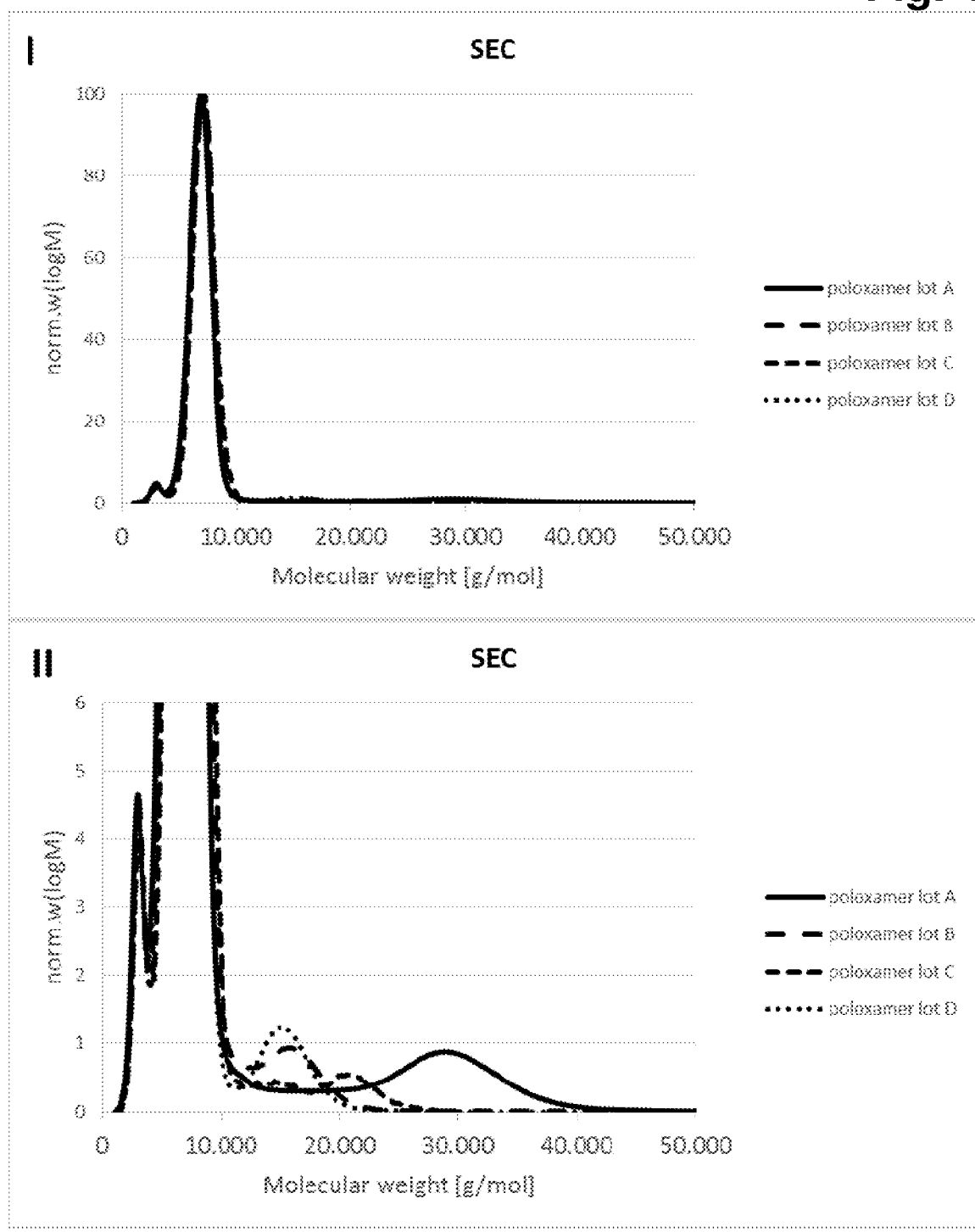
FIG. 4: Size exclusion chromatogram of poloxamer 188 lots A, B, C and D (I: full chromatogram, II: zoomed in).

Size exclusion chromatography measurements of poloxamer 188 lots A, B, C and D (FIG. 4). The high molecular weight component is observed between ~13 000 and 40 000 g/mol (FIG. 411).

Example 7b

Figure 5:
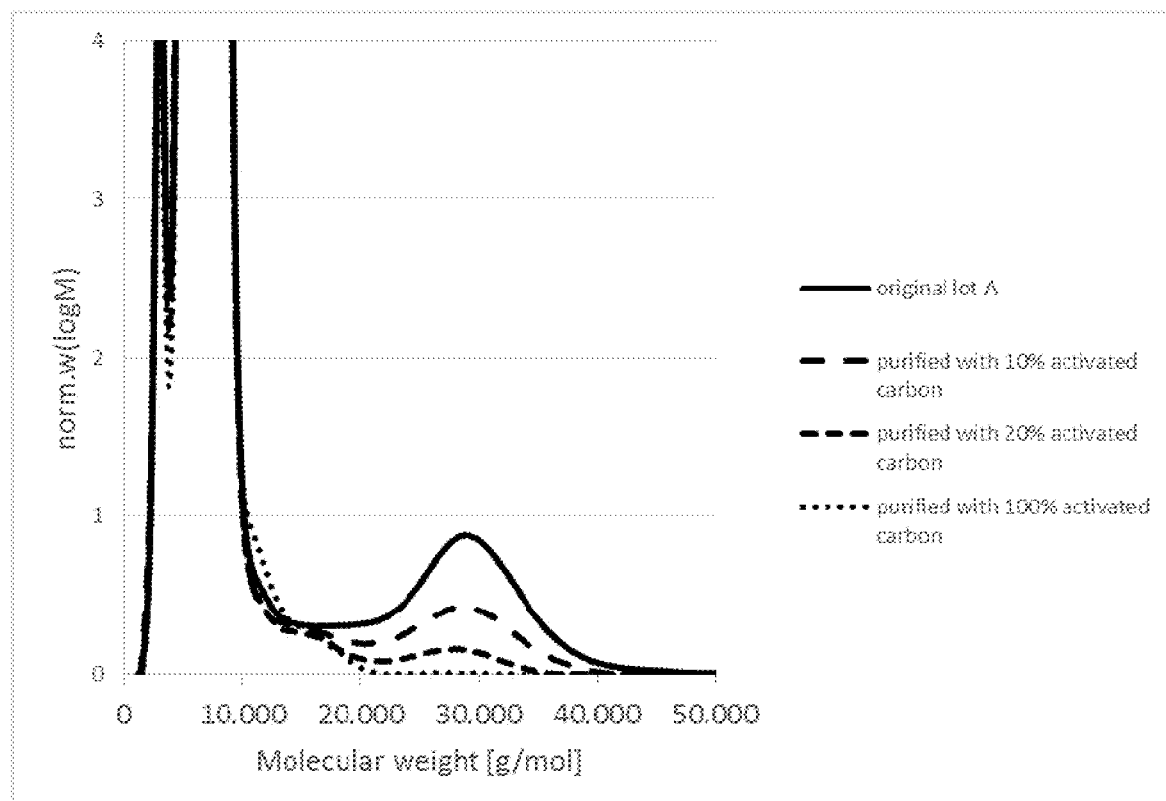
FIG. 5: Size exclusion chromatogram (zoomed in) of poor performing lot A (solid line) and after purification with 10, 20 and 100 wt. % activated carbon in ethanol/water (dashed lines) as described in example 2.

Size exclusion chromatography measurements of poor performing lot A purified with 10, 20 and 100 wt. % activated carbon in ethanol/water as described in example 2 (see FIG. 5). Purification removes the hydrophobic high molecular weight component at ~29 000 g/mol. With 100 wt. % activated carbon the hydrophobic high molecular weight component is completely removed. As a result cell viability is significantly improved so that the purified lot is suitable for the use in cell culture (Example 6b and FIG. 1).

Example 7c

Figure 6:
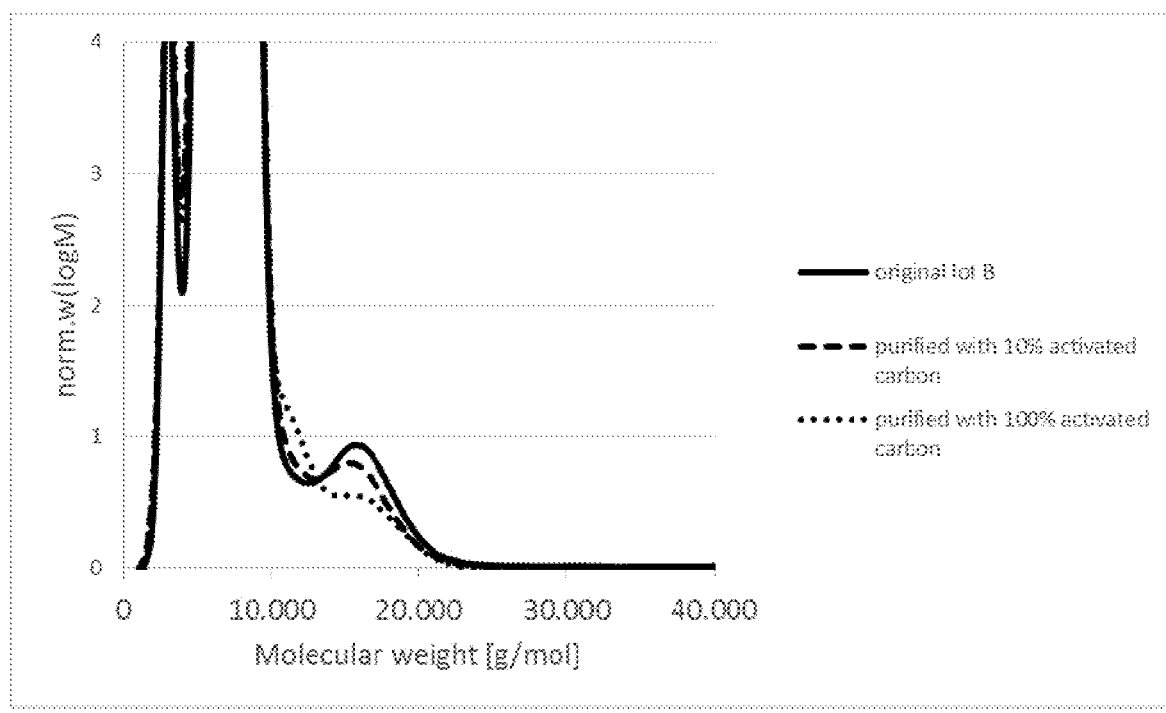
FIG. 6: Size exclusion chromatogram (zoomed in) of medium performing lot B (solid line) and after purification with 10 and 100 wt. % activated carbon in ethanol/water (dashed lines) as described in example 2.

Size exclusion chromatography measurements of medium performing lot B purified with 10 and 100 wt. % activated carbon in ethanol/water as described in example 2 (see FIG. 6). Purification removes the hydrophobic portion of the high molecular weight component at ~16 000 g/mol, which results in a significant decrease in intensity of the high molecular weight peak at ~16 000 g/mol. As a result cell viability is significantly improved so that the purified lot is suitable for the use in cell culture (Example 6b and FIG. 2).

Example 7d

Size exclusion chromatography measurements of well performing lot D treated with 10, 20 and 40 wt. % activated carbon in ethanol/water (dashed lines) as described in example 2 (see FIG. 7). No significant change in the high molecular weight peak (~15 000 g/mol) is observed after treatment with activated carbon. Small deviations observed for 40% activated carbon at ~11 000 g/mol can be attributed to residual activated carbon (not completely removed). This implies that the high molecular weight component in lot D does not have a higher hydrophobicity than poloxamer 188 and is thus not removed. High molecular weight components with similar hydrophobicity as poloxamer 188 (similar PPO/PEO ratio) have no negative effect on cell viability and cannot be removed by activated carbon (lot D, example 6b and FIG. 3).

Example 8

Purification of Poloxamer with Activated Carbon in Acetone in Flow Through 5.0 g spherical activated carbon (Felgenträger, surface area 1000-2000 m²/g, particle size 0.3-0.8 mm) were filled into a glass column (height 190 mm, inner diameter 10 mm) with a frit at the bottom end. The column was sealed at the bottom end, filled with acetone and carefully swiveled to remove air bubbles. The activated carbon bed in the column was left to settle overnight. 5.0 g poloxamer 188 lot A were dissolved in 300 ml acetone. The poloxamer solution was poured into the column and the bottom seal was removed. The poloxamer solution was collected after having passed through the column at a flow rate of 4.6 ml/min. The solvent was evaporated on a rotational evaporator until poloxamer was dry. Cell assay carried out as described in example 6. Performance of purified poloxamer lot:

| Poloxamer 188 lot | activated carbon [% w/w] | cell viability [%] | Improvement of viability after purification [%] |
|---|---|---|---|
| A | 100 | 88 | 80* |

*Improvement of viability calculated based on cell viability determined for poloxamer lot A described in example 6 (49%).

Purification of very poor performing lot A with activated carbon in acetone in flow through results in a significant improvement of cell viability. The improvement is better than in batch mode using standard activated carbon (see example 6e).

Example 9

Purification with Activated Carbon Using Shorter Mixing Time

Purification of poloxamer 188 lot A was carried out as described in example 2, but suspension was mixed for only 15 minutes.

| Poloxamer 188 lot | activated carbon [% w/w] | cell viability [%] | Improvement of viability after purification [%] |
|---|---|---|---|
| A | 100 | 93 | 90* |

*Improvement of viability calculated based on cell viability determined for poloxamer lot A described in example 6 (49%).

Purification of very poor performing lot A with 100 wt % activated carbon in ethanol/water with a mixing time of 15 minutes results in a significant improvement of cell viability, similar to the purification carried out with mixing overnight (see example 6b).

The invention claimed is:
1. A method for performing cell culture, comprising:
   a) providing poloxamers comprising hydrophobic, high molecular weight components;
   b) dissolving the poloxamers of step a) in a solvent and contacting them with activated carbon;
   c) removing the activated carbon and the solvent to obtain poloxamers having hydrophobic, high molecular weight components removed; and
   d) culturing cells in an aqueous culture medium comprising poloxamers obtained in step c).
2. The method according to claim 1, wherein the dissolved poloxamers are contacted with activated carbon for 2 to 24 hours.
3. The method according to claim 1, wherein activated carbon is removed by filtration and/or centrifugation.

4. The method according to claim 1, wherein the poloxamers provided comprise components that have a molecular weight over 13,000 g/mol.

5. The method according to claim 1, wherein the poloxamers are poloxamers which have an average molecular weight between 7,680 and 9,510 g/mol.

6. The method according to claim 1, wherein the activated carbon has a medium particle size between 2 and 800 µm.

7. The method according to claim 1, wherein the solvent is water, acetone, tetrahydrofuran or a mixture of ethanol and water.

8. The method according to claim 1, wherein the dissolved poloxamers are contacted with activated carbon for 1 to 24 hours.

9. The method according to claim 1, wherein the activated carbon is an activated carbon obtained by pyrolysis of an organic polymeric material.

10. The method according to claim 9, wherein the activated carbon is an activated carbon obtained by pyrolysis of polystyrene.

11. The method according to claim 9, wherein the dissolved poloxamers are contacted with activated carbon for 2 to 24 hours.

12. The method according to claim 9, wherein activated carbon is removed by filtration and/or centrifugation.

13. The method according to claim 9, wherein the poloxamers provided comprise components that have a molecular weight over 13,000 g/mol.

14. The method according to claim 9, wherein the poloxamers are poloxamers which have an average molecular weight between 7,680 and 9,510 g/mol.

15. The method according to claim 9, wherein the activated carbon has a medium particle size between 2 and 800 µm.

16. The method according to claim 9, wherein the solvent is water, acetone, tetrahydrofuran or a mixture of ethanol and water.

17. The method according to claim 9, wherein the dissolved poloxamers are contacted with activated carbon for 1 to 24 hours.

* * * * *